US010765787B2

United States Patent
Sutton et al.

(10) Patent No.: US 10,765,787 B2
(45) Date of Patent: Sep. 8, 2020

(54) COMPACT SOUND SUPPRESSING MUFFLER FOR BREAST VACUUM PUMPS

(71) Applicant: DAO Health, El Dorado Hills, CA (US)

(72) Inventors: Ben Sutton, Scotts Valley, CA (US); Dave Paul, Scotts Valley, CA (US); Dan Garbez, El Dorado Hills, CA (US)

(73) Assignee: DAO Health, El Dorado Hills, CA (US)

( * ) Notice: Subject to any disclaimer, the term of this patent is extended or adjusted under 35 U.S.C. 154(b) by 260 days.

(21) Appl. No.: 15/711,658

(22) Filed: Sep. 21, 2017

(65) Prior Publication Data

US 2019/0083688 A1    Mar. 21, 2019

(51) Int. Cl.
| | | |
|---|---|---|
| *A61M 1/06* | (2006.01) | |
| *A61M 1/00* | (2006.01) | |
| *F04C 29/06* | (2006.01) | |
| *F04C 25/02* | (2006.01) | |

(52) U.S. Cl.
CPC ............ *A61M 1/066* (2014.02); *A61M 1/007* (2014.02); *A61M 1/0066* (2013.01); *A61M 1/062* (2014.02); *F04C 29/065* (2013.01); *A61M 1/0074* (2013.01); *A61M 2205/42* (2013.01); *F04C 25/02* (2013.01); *F04C 29/063* (2013.01); *F04C 2220/10* (2013.01)

(58) Field of Classification Search
CPC .... A61M 1/066; A61M 1/007; A61M 1/0074; F04C 29/065; F04C 25/02; F04C 29/063
USPC ............................ 18/265, 230, 227, 228, 212
See application file for complete search history.

(56) References Cited

U.S. PATENT DOCUMENTS

| | | | | |
|---|---|---|---|---|
| 3,196,977 A | * | 7/1965 | Sanders ..................... | F01N 1/10 181/256 |
| 6,305,493 B1 | * | 10/2001 | Laimbock ................. | F01N 1/02 181/230 |
| 6,935,461 B2 | * | 8/2005 | Marocco ................... | F01N 1/02 181/212 |
| 7,537,083 B2 | * | 5/2009 | Frederiksen .............. | F01N 1/04 181/212 |
| 7,789,194 B2 | * | 9/2010 | Lathrop ............ | A61M 16/0066 181/212 |
| 7,810,609 B2 | * | 10/2010 | Sikes ........................ | F01N 1/24 181/246 |

(Continued)

*Primary Examiner* — Forrest M Phillips
(74) *Attorney, Agent, or Firm* — Rockman Videbeck & O'Connor

(57) ABSTRACT

A sound suppression system for reducing or eliminating sound produced by the operation of a breast vacuum pump includes a sound suppressing muffler assembly having an air entry port adapted to communicate with an air outlet port of a vacuum pump or other air flow generating device. The sound suppressing muffler assembly also includes a muffler housing defining an internal space communicating with the air entry port, and an opening in the housing leading to atmosphere. The muffler housing has a tortuous air path in the muffler housing. In one embodiment, sound absorbing porous foam structure is disposed in the tortuous air path. The at least one sound absorbing porous structure absorbs sound energy from the air as the air moves through the at least one air path toward the opening in the muffler housing. In further embodiments, a tortuous air path is provided between an air entry port and an opening to atmosphere in the muffler assembly.

10 Claims, 5 Drawing Sheets

(56) References Cited

U.S. PATENT DOCUMENTS

| | | | | |
|---|---|---|---|---|
| 8,006,801 | B2* | 8/2011 | Christoffers | B60T 17/008 181/230 |
| 8,215,448 | B2* | 7/2012 | Harting | B60T 17/008 181/229 |
| 8,302,732 | B2* | 11/2012 | Gorke | F01N 1/084 181/212 |
| 2002/0027041 | A1* | 3/2002 | Czabala | F04C 29/065 181/229 |
| 2004/0050618 | A1* | 3/2004 | Marocco | F01N 1/02 181/248 |
| 2005/0103566 | A1* | 5/2005 | Sterling | B23B 47/00 181/230 |
| 2005/0269152 | A1* | 12/2005 | Sellers, II | B25F 5/00 181/230 |
| 2008/0289900 | A1* | 11/2008 | Christoffers | B60T 17/008 181/258 |
| 2010/0270103 | A1* | 10/2010 | Huff | F01N 1/02 181/266 |

* cited by examiner

COMPACT SOUND SUPPRESSING MUFFLER FOR BREAST VACUUM PUMPS

FIELD OF THE INVENTION

This invention relates to the field of human breast milk pumping and storage devices, and more specifically, a compact sound suppressing device to reduce or eliminate noise emanating from a breast pump system.

BACKGROUND OF THE INVENTION

Breast pumps are well known, but the field of naturally shaped breast milk collection devices with self-contained breast milk reservoirs which work with breast pumps and can be used discreetly by fitting them within a woman's brassiere, often under ordinary clothing so that a woman can use a breast pump around others discreetly, is relatively new. The only known devices in this field, upon which this invention improves, are taught in U.S. Pat. Nos. 7,559,915; 8,118,772, and 8,702,646 (Dao, Garbez), the disclosures of which patents are incorporated by reference herein.

The above-mentioned patents disclose a milk collecting reservoir generally cup-shaped to fit into a lactating woman's brassiere, which reservoir is adapted to be disconnected from a pump and emptied when full after hands-free operation, whereby the milk can be transferred to a feeding or milk storage device such as a baby bottle, pliable storage bag, or other suitable container.

Prior to the development and use of breast pump devices with self-contained breast milk reservoirs, breast pumping by new mothers was conducted in private, where noise produced by the breast pump assemblies was not a problem. As a result the reduction or elimination of noise while expressing milk from a mother's breast has never been a design focus in the development of breast pump systems. However, with the introduction of breast pump devices with self-contained reservoirs, breast milk pumping and expressing now takes place discreetly, but in public places, such as the desk or office of a lactating working mother. In these latter situations, it is desirable that the milk pumping system produces little or no noise so as not to distract nearby personnel, or to draw unnecessary attention to the mother using the breast milk pumping device.

Sound is a form of energy created when air is caused to vibrate, such as when air is forced through a tube at rapidly changing pressures. This energy travels outward in the environment away from the sound source since the air in the environment carries sound waves, and objects as well as the air in the environment vibrate in sympathy until the remaining energy reaches one's ears. An object of sound suppression techniques is to interrupt and/or divert the chain of vibrating air flow at some point between the source of the vibration and one's ears.

Since sound comprises long-wavelength sound waves, sound energy can easily move through most solids and emerge loudly on the other side of the solid mass as the air on the other side of the solid mass vibrates again. Noise can be suppressed by preventing the direct movement or flow of air from the air outlet of a breast pump vacuum system to the atmosphere surrounding the breast pump vacuum system, thus creating an indirect air flow. One way to suppress noise in such system is to interfere with the path the sound is likely to take before reaching one's ears through the use of absorbent rubbery or porous foam material that "soaks up" or absorbs sound energy before the sound energy reaches the environment. Such sound absorbent materials include, among others, thread-like glass fiber materials, porous foam, and neoprene rubber. Baffle structures may also be used to divert the path of the moving air, thus interfering with the direct movement of air from the air outlet to the atmosphere.

Therefore, an object of the present invention is to provide a compact noise suppressing or muffler system for reducing or eliminating noise emanating from a breast pump assembly. In addition, the compact construction of the presently disclosed and described device may have other applications where it is desirable to reduce or eliminate noise generated by a small or medium sized air pump system.

SUMMARY OF THE INVENTION

A sound suppression system for reducing or eliminating sound produced by the operation of a breast vacuum pump includes a sound suppressing muffler assembly adapted to be attached to and communicate with an air outlet of the vacuum pump. The sound suppressing muffler includes a muffler structure defining an internal space communicating with the vacuum pump air outlet at one end and with atmosphere at another end. The sound suppressing muffler assembly also includes a tortuous air path creating an indirect flow of air through the sound suppressing muffler assembly to atmosphere, the indirect airflow suppressing the noise energy produced by air moving through the tortuous path.

DETAILED DESCRIPTION OF THE ILLUSTRATED EMBODIMENTS

The presently disclosed compact sound suppression device will be more fully understood by reference to the following drawings of the illustrated embodiments, which drawings are for illustrative purposes only and are not to be considered as limiting the scope of the claims.

The compact breast pump noise suppressing and tortuous path muffler system embodiments disclosed herein are adapted to be used in conjunction with a combination breast vacuum pump and drive motor, as described below. However, the disclosed tortuous path noise suppressing and muffler system can also be used in association with other apparatus where air flow noise reduction or elimination is desired to be achieved.

Figure 1:
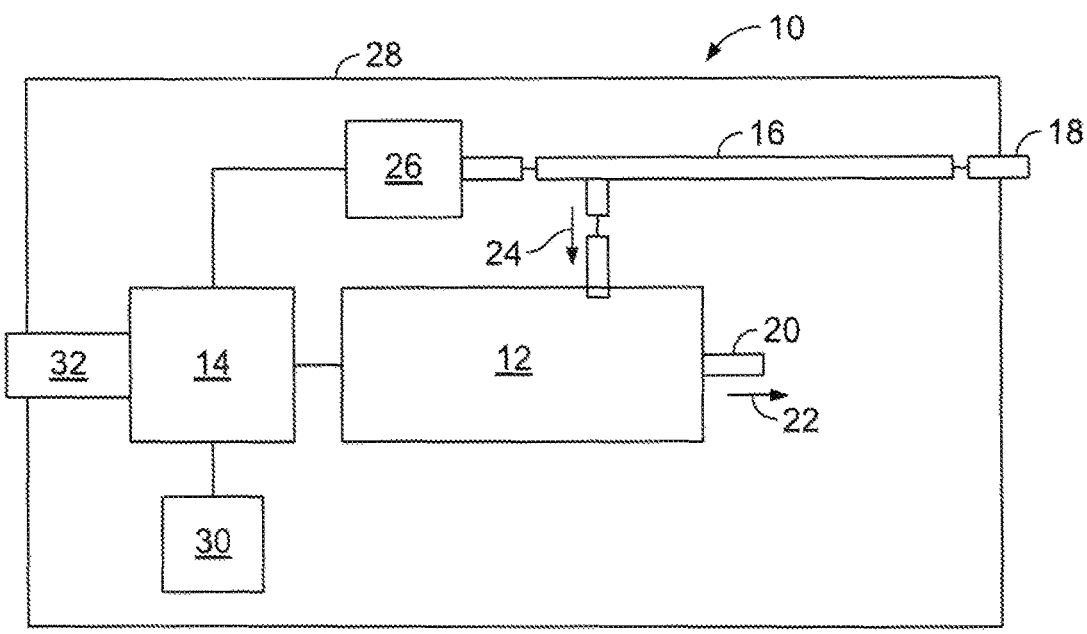
FIG. 1 is. a schematic diagram of one embodiment of a breast pump operating assembly adapted to be connected to a tubing connection port of a breast milk reservoir system.

A combination breast pump and drive motor assembly 10 is generally illustrated by the schematic drawing of FIG. 1. Referring to FIG. 1, a vacuum pump and drive motor 12 is controlled by circuit and control board 14 to create a vacuum in the tubing 16. Tube 16 is connected at end 18 to a breastmilk reservoir collection system (not shown). Air is relieved to atmosphere from pump outlet 20 as shown by arrow 22. Air from the breast milk collection system is pulled in only one direction through tubing 16 by pump 12, as shown by arrow 24. A solenoid valve comprises venting device 26, where venting device 26 is attached to the single vacuum tubing 16 of the pump system 10. The solenoid valve 26 is located in the pump and motor housing 28 and is operated by the circuit and control board 14. Vacuum in the milk reservoir system is released when venting device 26 opens tube 16 to atmosphere, cyclically relieving vacuum in the reservoir via the vacuum line 16 and through solenoid outlet 26 from atmosphere.

The circuit and control board 14 alternately turns the drive motor and vacuum pump 12 on and off, with the solenoid 26 alternately shut, then open. The circuit and control board also controls the charging of battery 30 via charging port 32. The pump 12 pulls air through tubing 16 when the vacuum pump 12 is "on." When the pump 12 is "off," solenoid valve 26 opens to let air from the atmosphere into tubing 16 and relieves the vacuum in tube 16. Solenoid valve 26 then closes, and pump 12 is turned "on" again by control board 14 to create a vacuum in tubing 16. The alternate cycles of suction and normal air pressure are created by shutting off the motor and vacuum pump 12 and opening the venting device 26, and then closing the venting device 26 and starting the motor and pump again. Thus, the motor and pump are shut off, and solenoid valve/venting device 26 is opened to "cancel" the built-up vacuum. Then the valve 26 is shut, and the motor and vacuum pump 12 are activated again to generate vacuum in line 16 for the next cycle.

During alternating or cyclic release of air to the atmosphere through pump outlet 20, noises are created in outlet 20 due to the rapid changes in air flow, and consequent fluttering of the air in the channel formed by pump outlet 20. Since the pump and drive motor assembly 10 is adapted to be used with a self-contained milk collecting reservoir system while the lactating mother is in a public or semi-private area, it has been found to be desirable to minimize or eliminate the noise forming in pump outlet 20. To this end, the compact sound suppressing muffler embodiment described below has been developed.

Figure 2:
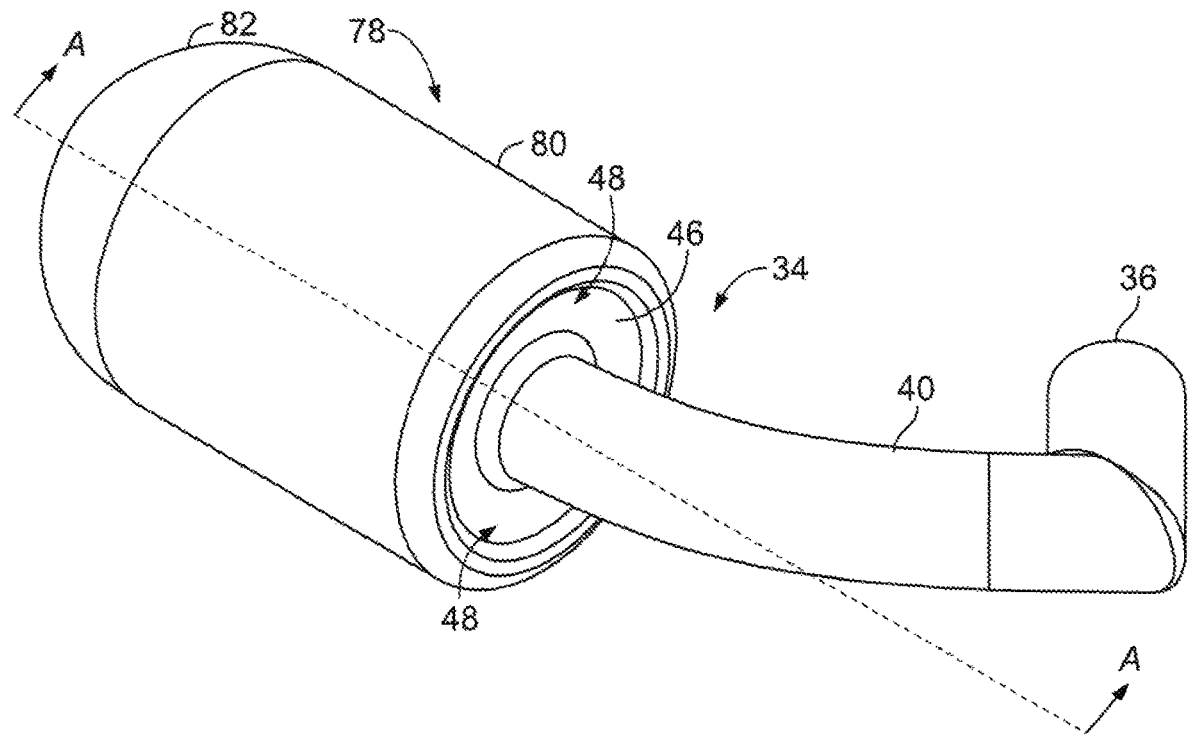
FIG. 2 is a front perspective view of the presently disclosed compact muffler assembly.
Figure 3:
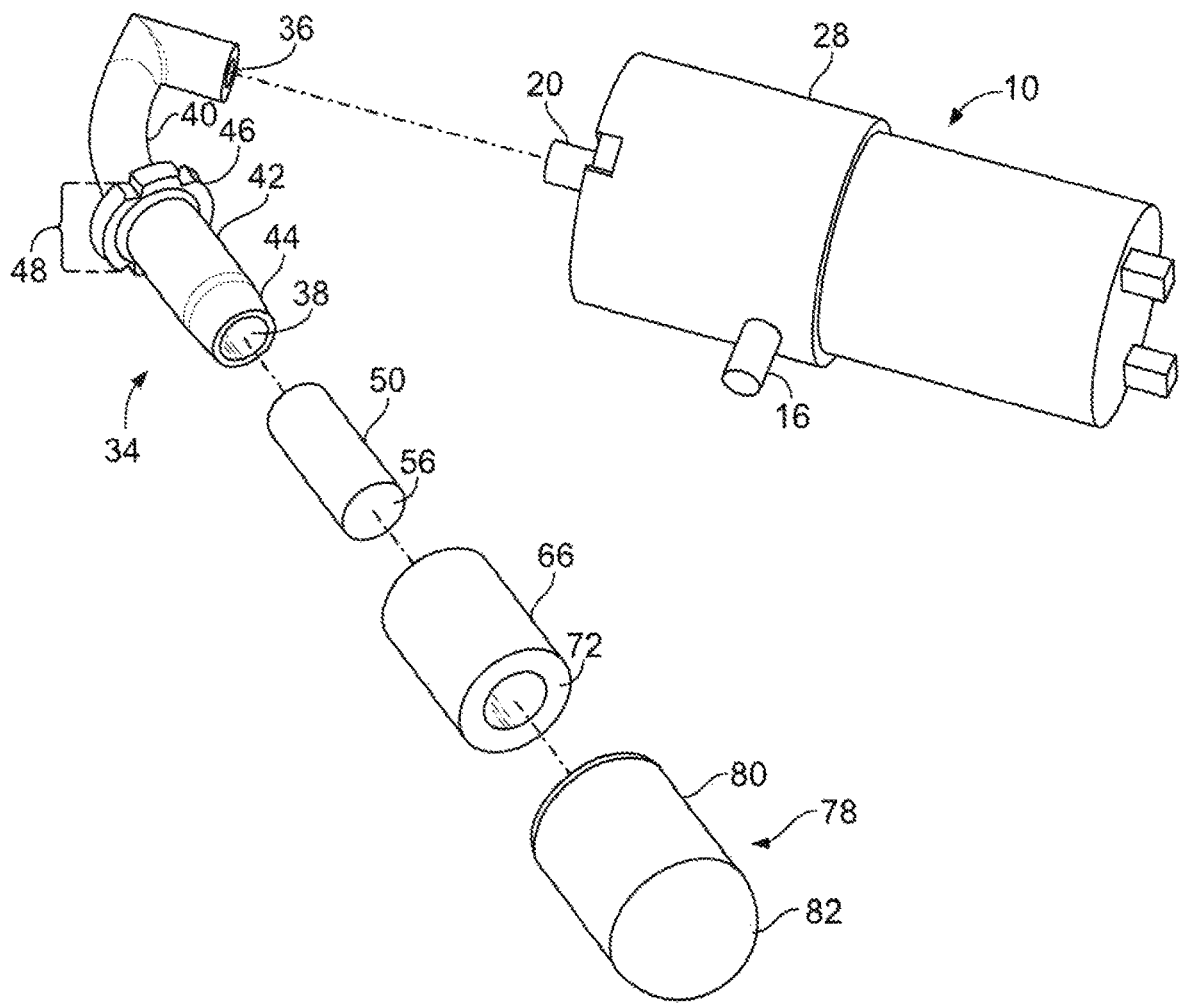
FIG. 3 is an exploded perspective view of the compact muffler assembly of FIG. 2, also including a perspective side view of a typical breast pump and pump motor housing to which the compact muffler assembly is adapted to be attached.

Referring to FIGS. 2 and 3, the compact sound suppressing muffler is generally designated by the numeral 34. Muffler 34 at one end comprises a hollow entry port 36, best seen in FIG. 3, communicating with an internal passage 38 in muffler tube 40. Referring to FIG. 3, the end of muffler tube 40 extending away from entrance port 36 comprises a hollow tubular support 42 firmly attached to tube 40. Tube support 42 includes a tapered end 44 for purposes to be explained. A radially extending circular flange 46 having a plurality of openings or notches 48 is fixed to tubular support 42 at the end of support 42 opposite tapered end 44. Muffler tube 40 and hollow tubular support 42 are typically constructed of silicone, or some other similar sturdy, soft, elastic and dense material.

Figure 4:
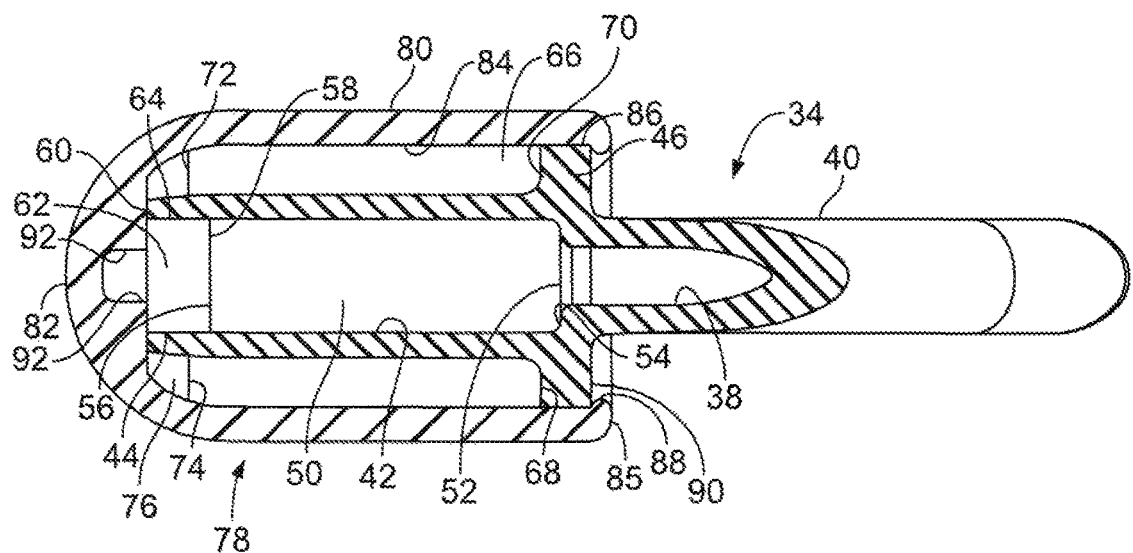
FIG. 4 is a front section view of the compact muffler assembly, taken along line A-A of FIG. 2.

Referring to FIGS. 3 and 4, a solid cylinder 50 of a porous foam, or equivalent material of various geometric and sound energy absorbent properties that allows air to pass through the cylinder 50, is located to extend axially in the hollow portion of tubular support 42. One end 52 of cylinder 50 abuts against flange 54 where internal passage 38 enters hollow tubular support 42. An opposite end 56 of cylinder 50 terminates at 58 before reaching end 60 of hollow tubular support 42, creating a cavity 62 in the outward end 64 of support 42.

A hollow cylinder 66, also comprised of a porous foam that allows air to pass through the cylinder 66 or an equivalent material, circumscribes the outer surface of hollow tubular support 42. Hollow cylinder 66 extends axially around tubular support 42, and a first end 68 of hollow cylinder 66 abuts against a radial surface 70 of flange 46, as seen in FIG. 4. However, the end 68 does not extend over notches 48 in flange 46, thereby allowing air to freely flow through openings or notches 48. The opposite end 72 of hollow cylinder 66 terminates axially at 74, defining a cavity 76 between end 74 of cylinder 66, tapered surface 44 and an internal portion of cap 78. End 72 of hollow cylinder 66 extends partially over tapered surface 44 which aids in properly locating and holding hollow cylinder 66 in place over tubular support 42.

Figure 5:
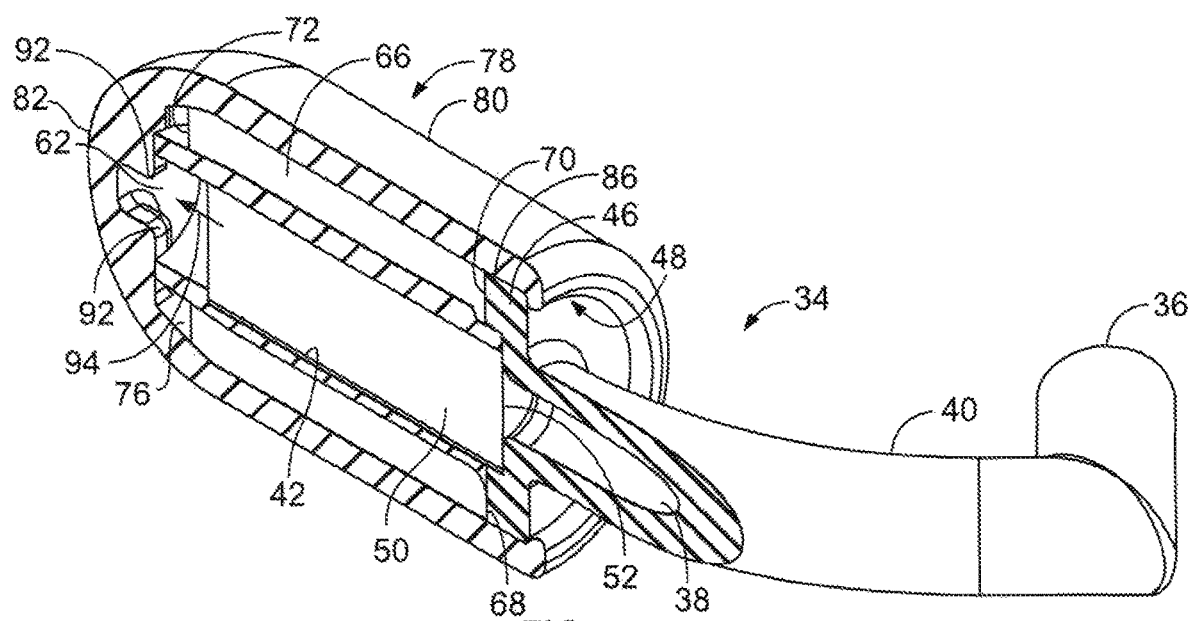
FIG. 5 is a perspective side frontal section view of the compact muffler assembly, taken along line A-A of FIG. 2.

Cap 78 is adapted to extend over and provide a cover for the compact sound suppressing tortuous path muffler 34. In the illustrated embodiment of FIGS. 2-5, cap 78 is comprised of a sturdy material such as silicone, hard plastic, or other suitable materials as are known in the art. Cap 78 has an outer cylindrical surface 80 and a somewhat hemispherical outer end surface 82. As illustrated in FIGS. 4 and 5, cap 78 has a hollow interior 84 that removably and snugly fits at one end 85 on the outer circumferential surface 86 of flange 46 of tubular support 42. An inwardly directed circular flange 88 is formed on end 85 of cap 78, and flange 88 is adapted to engage a portion of surface 90 of flange 46, thereby providing a removable snap fit attachment between cap 78 and flange 46.

As seen in FIGS. 4 and 5, hollow interior 84 of cap 78 abuts the outer surface of hollow foam cylinder 66 and secures cylinder 66 in position on tubular support 42. The cavity 76 adjacent end 72 of foam cylinder 66 is formed by spaced apart abutments 92 that provide an air path 94 from foam cylinder 50, into cavity 76, and into end 72 of foam cylinder 66.

In operation, entry port 36 of compact sound suppressing muffler 34 is tightly, and if desired removably, attached to pump outlet 20 (FIGS. 1 and 3). As vacuum pump and drive motor 12 operate, air cyclically flows from pump outlet 20 through internal passage 38 of hollow tubular support 42. Referring to FIGS. 4 and 5, the air in internal passage 38 passes through porous cylinder 50 to cavity 62. Since there are spaces in cap 78 connecting cavity 62 with cavity 76, the air flowing through foam cylinder 50 reverses direction, and continues its flow through hollow foam cylinder 66 until the air reaches radial surface 70 of flange 46. The air then passes out of openings or notches 48 and into the atmosphere.

As explained above, the air from pump outlet 20 passes through a circuitous or tortuous route as the air passes through sound suppressing muffler 34.

As the air passes from internal passage 38 and flows through cylindrical foam mass 50 in a first direction, the sound waves caused by the air movement are partially absorbed by foam mass 50. The air exiting the end 56 of foam mass 50 enters cavity 62 and then reflects off of the internal surfaces of cap 78 until the air reaches cavity 76. From cavity 76, the air passes through cylindrical foam mass 66 in a second direction, where the foam material 66 adds further absorption of the sound wave energy created by the moving air. As the air passing through cylindrical foam mass 66 reaches radial surface 70 of flange 46, the air escapes through openings or notches 48 and into the surrounding atmosphere. The air escaping through openings or notches 48 has lost most, if not all, of its vibrating energy as a result of passing through foam mass 50 and cylindrical foam mass 66. As a result, the noise created by the vibration of air leaving pump outlet 20 is substantially reduced or altogether eliminated, causing less or no noise to be created from the operation of the vacuum pump 12.

Figure 6:
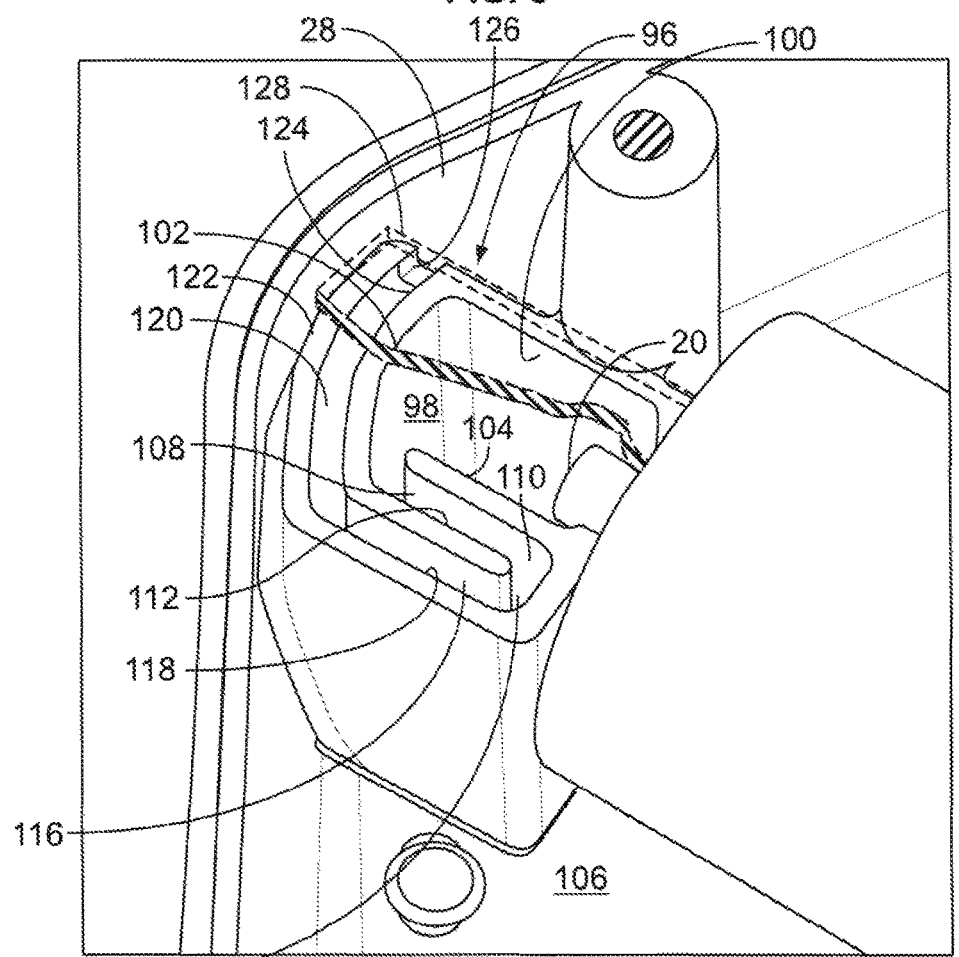
FIG. 6 is a perspective detail top view of a further embodiment of the present invention having a tortuous air path formed by a first baffle system communicating with an outlet of the breast pump air outlet, and a cover for the baffle system partially shown.
Figure 7:
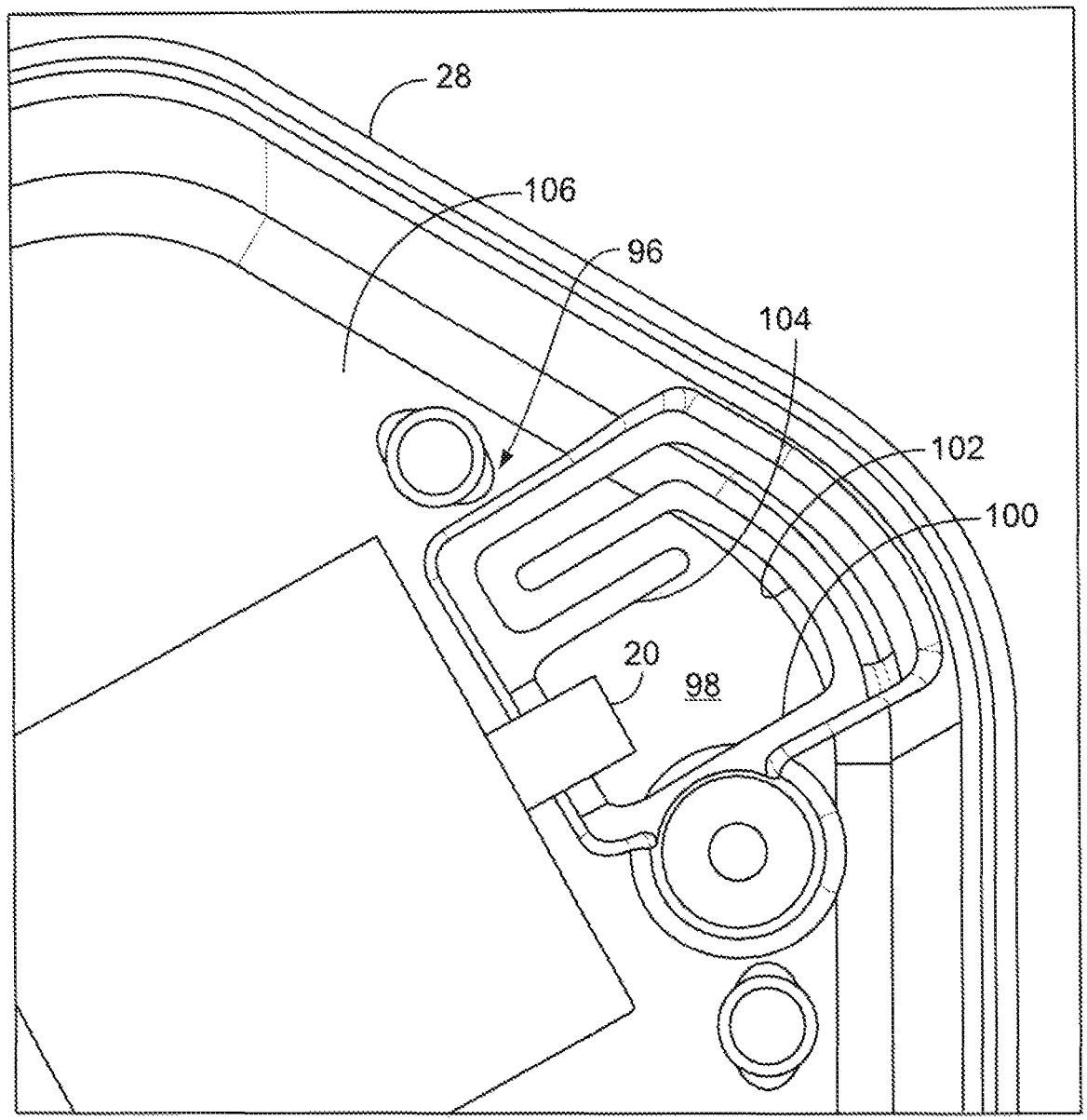
FIG. 7 is a top view of the first baffle system illustrated in FIG. 6.

An additional embodiment of the present invention is illustrated in FIGS. 6 and 7, comprising a sound suppression baffle system 96 molded into the body of motor housing 28 (FIG. 3). As seen in FIGS. 6 and 7, pump outlet 20 communicates with a first chamber 98 defined by walls 100, 102, and 104. Each wall 100, 102 and 104 is integrally molded at one end with a sidewall 106 of housing 28. A cover plate 128, partially shown in FIG. 6, closes the upper portions of baffle system 96 to ensure that chamber 98 is air tight, except for opening 108 that leads to second chamber 110 defined by wall 104 and wall 112. Chamber 110 also includes an opening 114 that communicates with a third chamber 116 formed by wall 112 and wall 118.

A fourth chamber 120 is defined by wall 102 and wall 122. A closure wall 124 extends between walls 102 and 122, and includes a vent port 126 that allows air to pass out of fourth chamber 120 to atmosphere, as will be explained. As can be seen in FIGS. 6 and 7, first, second, third and fourth chambers 98, 110, 116 and 120 provide a tortuous path for air leaving pump outlet 20 to travel before exhausting to atmosphere inside housing 28. As seen in FIG. 6, a cover 128 (shown in breakaway) is disposed over one end of chambers 98, 110, 116 and 120 so that air leaving pump outlet 20 is confined to travel along the tortuous path created by the four chambers.

Figure 8:
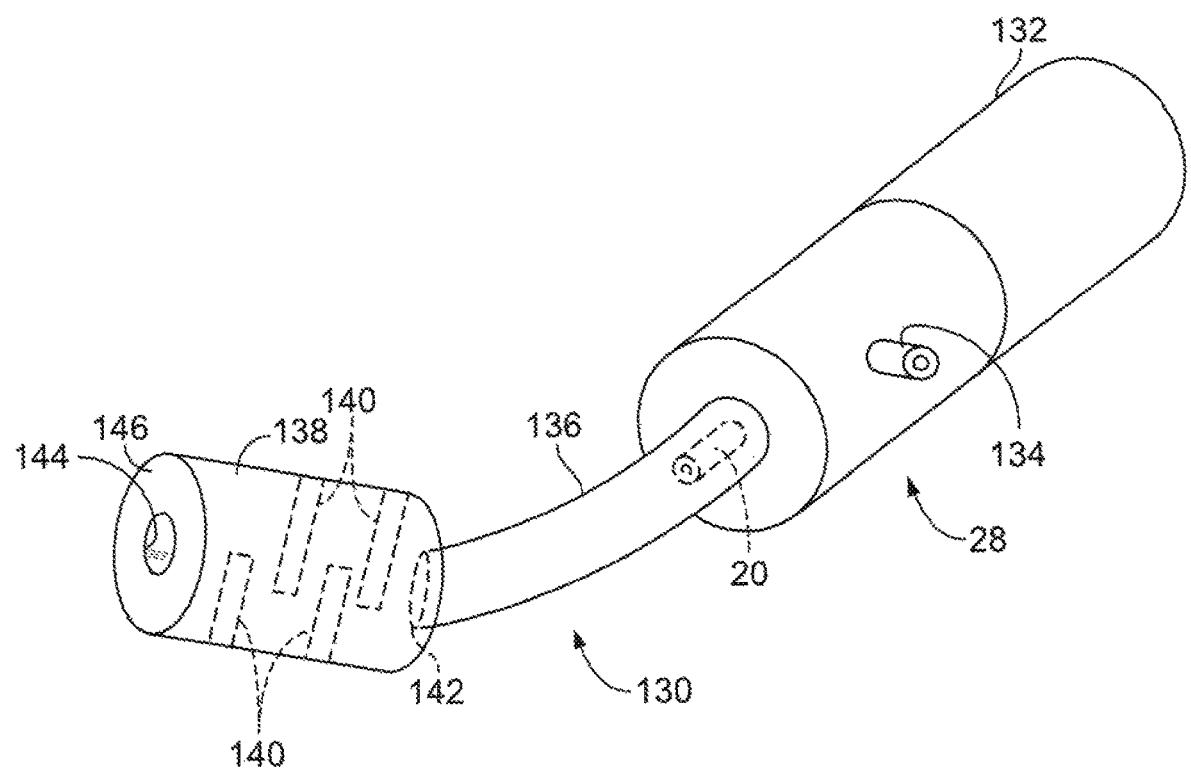
FIG. 8 is a perspective view of a further embodiment of the present invention, having a baffle system assembly providing a tortuous path for the air exiting the breast pump vacuum system and flowing to atmosphere.

In operation, air exhausting from pump outlet 20 in the embodiment of FIGS. 7 and 8 sequentially passes through chambers 98, 110, 116 and 120 until the air is expelled through vent port 126 to atmosphere.

As the air passes through the chambers, its direct travel is interrupted several times, mitigating and reducing the strength or level of airborne sound. The walls forming the chambers 98, 110, 116 and 120 are solid in this embodiment, and reverberation of the moving air is eliminated. As a result of the reduction of the sound energy of the air passing tortuously through the chambers 98, 110, 116 and 120, the sound produced by air escaping pump outlet 20 is significantly reduced.

A third embodiment of the presently disclosed compact sound suppressing muffler for breast vacuum pumps is illustrated in FIG. 8, where a hollow tubing and muffler structure 130 communicates with air exhausting from pump outlet 20 that extends outward from pump housing 28. Hollow tubing and muffler structure 130 can be permanently or removably attached to pump outlet 20.

A motor to drive the pump located in housing 28 is disposed in motor housing 132. Pump suction port 134 communicates with a self-contained breast milk reservoir system (not shown).

Hollow tubing and muffler structure 130 includes a hollow tube portion 136 communicating with pump outlet 20. The end of the tube portion 136 opposite from pump outlet 20 comprises an in-line hollow housing 138, with a plurality of baffle plates 140 located in hollow housing 138. An entrance aperture 142 permits one end of hollow tube portion 136 to communicate with the interior of hollow housing 138. Opposite entrance aperture 142 of structure 130 at end 146 is an exit port 144 through which air exhausts to atmosphere, as will be explained.

In operation, the pump of the embodiment of FIG. 8 transmits air from pump outlet 20, into hollow tube portion 136, and into hollow housing 138 via entrance aperture 142. The air entering hollow housing 138 then passes through the tortuous path created by staggered baffle plates 140. Upon reaching the end 146 of hollow housing 138, the air passes through exit port 144 to atmosphere. As a result of traveling through the tortuous path created by baffle plates 140, the air passing through hollow housing 138 loses energy, and the sound created by the moving air is significantly reduced, as explained previously.

Figure 9:
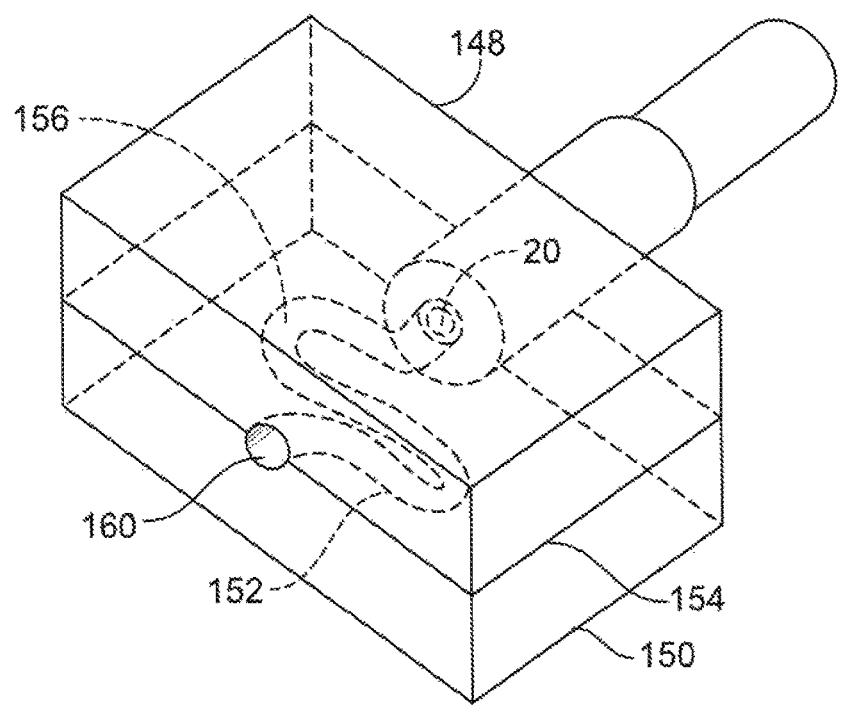
FIG. 9 is a perspective schematic view of another embodiment of the present invention that includes a tortuous air flow path formed in an assembly formed in foam block halves.

A fourth embodiment of the presently disclosed sound suppressing apparatus is illustrated in FIG. 9, where a pair of foam block halves 148, 150 are either permanently or removably in communication with pump outlet 20. When foam block halves 148, 150 are placed in contact with each other, as shown in FIG. 9, a tortuous path 152 for air exhausted from pump outlet 20 is created through the plane of juncture 154 between foam block halves 148, 150. Each of foam block halves 148, 150 include non-linear channel halves 156, 158, which form substantially circular tortuous path 152 when the foam block halves are placed adjacent one another, as seen in FIG. 9.

Referring to FIG. 9, when air passes through pump outlet 20, the air passes through tortuous path 152 and exits air vent 160 to atmosphere. As explained previously with regard to the embodiment of FIGS. 6-8, the air passing through tortuous path 152 loses energy, significantly reducing the sound created by the moving air. Additionally, any sound energy produced in tortuous path 152 is absorbed by foam block halves 148, 150 thus reducing or eliminating sound energy created in the foam block halves 148, 150 adjacent tortuous path 152. In a further embodiment of the structure disclosed in FIG. 9, a single block of foam material can be utilized, with tortuous path 152 formed in and through the single foam block.

Each of the embodiment of the presently disclosed sound suppression system for breast vacuum pumps provides a combination of effective sound suppression with minimum hindrance to air flow. The sound suppressing materials used in the embodiments of FIGS. 1-5 and 9 can be formed from a variety of suitable materials, form low to high density, with various geometric and sound energy absorbent properties.

The foregoing description of illustrated embodiments of the disclosed apparatus has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed:

1. A sound suppression system for reducing or eliminating sound produced by the operation of a breast vacuum pump, comprising:
   a. a sound suppressing muffler assembly having an air entry port, said air entry port adapted to communicate with an air outlet port of said breast vacuum pump;
   b. said sound suppressing muffler assembly including a muffler housing defining an internal space communicating with said air entry port;
   c. said muffler assembly having an opening to atmosphere;
   d. at least one non-linear, reciprocal tortuous air path in said muffler assembly;
   e. said non-linear, reciprocal tortuous air path creating an indirect flow of air through said non-linear, reciprocal tortuous air path to atmosphere, said indirect air flow suppressing noise energy produced by air moving through said non-linear, reciprocal tortuous air path; and
   said non-linear, reciprocal tortuous air path comprising at least one sound-absorbing porous foam structure disposed in said at least one non-linear, reciprocal tortuous air path, said at least one sound absorbing porous foam structure absorbing sound energy from said air as said air moves through said non-linear, reciprocal tortuous air path toward said opening in said muffler housing.

2. The sound suppression system of claim 1, wherein:
   said non-linear, reciprocal tortuous air path extends through at least one foam block assembly.

3. The sound suppression system of claim 2, wherein:
   said at least one foam block assembly comprises two foam block structures in contact with each other at a plane of juncture;
   each said foam block structure including a non-linear tortuous, reciprocal, air channel half, each of said channel halves forming said reciprocal, non-linear tortuous air channel through the foam block structures, the tortuous air channel extending from said air entry port to said opening to atmosphere.

4. A sound suppression system for reducing or eliminating sound produced by the operation of a breast vacuum pump, comprising:
   a. a sound suppressing muffler assembly having an air entry port, said air entry port adapted to communicate with an air outlet port of said vacuum pump;
   b. the sound suppressing muffler assembly including a first path for air to pass through upon emerging from said air entry port;
   c. the sound suppressing muffler assembly including a second path for the air emerging from the first path to pass through, said second path circumscribing said first path;
   d. the sound suppressing muffler assembly also including at least one opening in a muffler housing, the air in said second path passing through said at least one opening to atmosphere;
   e. said first and second paths absorbing sound energy from said air as said air moves through said first and second paths;
   f. at least one of said first and second paths includes a low density porous foam structure through which said air passes, said low density porous foam structure absorbing said sound energy as said air moves through said first path.

5. The sound suppression system of claim 4, wherein:
   each of said first path and said second path includes a first and second porous foam structure, respectively, through which said air passes, said first and second porous foam structure in each said path absorbing sound energy as air moves through each of said paths, said second porous foam structure circumscribing said first porous foam structure.

6. The sound suppression system of claim 5, wherein said muffler housing includes:
   a hollow tubular support having a hollow axial portion communicating with said air entry port;
   said first porous foam structure disposed in said hollow axial portion of said hollow tubular support, said first porous foam structure absorbing sound energy from said air as said air moves through said first porous foam structure.

7. The sound suppression system of claim 5, wherein said muffler housing includes:
   a hollow tubular support having an outer surface disposed in said muffler housing, said outer surface defining a space between an inner surface of said muffler housing and said outer surface of said hollow tubular support,
   said second porous foam structure disposed in said space between the inner surface of said muffler housing and said outer surface of said hollow tubular support, said second porous foam structure absorbing sound energy from said air as said air moves through said second porous foam structure.

8. A sound suppression system for reducing or eliminating sound produced by the operation of a breast vacuum pump, comprising:
   a sound suppressing muffler assembly having an air entry port, said air entry port adapted to communicate with an air outlet port of said vacuum pump;
   said sound suppressing muffler assembly having a housing defining a first internal space communicating with said air entry port and a second internal space communicating with an opening in said housing, said opening communicating with atmosphere, said second internal space circumscribing said first internal space;
   a first porous foam sound absorbing structure disposed in said first internal space, and a second porous foam sound absorbing structure disposed in said second internal space;
   said first and second internal spaces communicating with each other, air passing through said first internal space in a first direction, and next passing through said second internal space in a second direction, and next passing through said opening in said housing;
   said housing including a hollow tubular support, a hollow portion of said tubular support defining said first internal space, said first porous foam sound absorbing structure disposed in said first internal space;
   said housing further including a second internal space defined by an outer circumference of said hollow tubular support and an internal surface of said housing, said second porous foam sound absorbing structure disposed in said second internal space;
   said first and second porous foam sound absorbing structures absorbing sound energy as said air passes through said air entry port, through said first and second porous foam sound absorbing structures, and through said opening in said housing to atmosphere.

9. A sound suppression system for reducing or eliminating sound produced by a source of air flow, comprising:

a sound suppressing muffler assembly having an air entry port, said air entry port adapted to communicate with an air outlet port of an air flow generating device;

said sound suppressing muffler assembly having a housing defining a first internal space communicating with said air entry port and a second internal space communicating with an opening in said housing, said opening leading to atmosphere and said second internal space circumscribing said first internal space;

a first porous foam sound absorbing structure disposed in said first internal space, and a second porous foam sound absorbing structure disposed in said second internal space;

said first and second internal spaces communicating with each other, air passing through said first internal space in a first direction, and next passing through said second internal space in a second direction, and next passing through said opening in said housing;

said housing including a hollow tubular support, a hollow portion of said tubular support defining said first internal space, said first porous foam sound absorbing structure disposed in said first internal space;

said second internal space defined by an outer circumference of said hollow tubular support and an internal surface of said housing, said second porous foam sound absorbing structure disposed in said second internal space;

said first and second porous foam sound absorbing structures absorbing sound energy as said air passes through said air entry port, through said first and second porous foam sound absorbing structures in different directions, and through said opening in said housing to atmosphere.

10. The sound suppressing system of claim 9, wherein:

said first and second porous foam sound absorbing structures extend coaxially in said housing.

\* \* \* \* \*